United States Patent
Tanaka et al.

(10) Patent No.: US 6,787,657 B2
(45) Date of Patent: Sep. 7, 2004

(54) OPTICALLY ACTIVE EPOXYPROPIONATE DERIVATIVE, INTERMEDIATE THEREOF AND PROCESSES FOR THEIR PRODUCTION

(75) Inventors: Akinori Tanaka, Shinnanyo (JP); Takumi Kagawa, Shinnanyo (JP)

(73) Assignee: Tosoh Corporation, Yamaguchi-ken (JP)

( * ) Notice: Subject to any disclaimer, the term of this patent is extended or adjusted under 35 U.S.C. 154(b) by 9 days.

(21) Appl. No.: 09/788,369

(22) Filed: Feb. 21, 2001

(65) Prior Publication Data

US 2001/0020106 A1 Sep. 6, 2001

(30) Foreign Application Priority Data

Feb. 24, 2000 (JP) ............................................. 12-052268
Jun. 8, 2000 (JP) ............................................. 12-177153

(51) Int. Cl.[7] ...................... C07D 303/16; C07D 301/02
(52) U.S. Cl. ........................ 549/539; 549/548; 549/549
(58) Field of Search ................................. 549/539, 548, 549/549

(56) References Cited

FOREIGN PATENT DOCUMENTS

| EP | 0062772 | 10/1982 |
|---|---|---|
| JP | 57142974 | 9/1982 |
| JP | 58099429 | 6/1983 |
| JP | 58099430 | 6/1983 |
| JP | 60013776 | 1/1985 |
| JP | 01226881 | 9/1989 |
| JP | 06287183 | 10/1994 |

OTHER PUBLICATIONS

Bull Chem. Soc. Jpn, 55, 3208–3211 (1982) Watanabe et al Aldol Condensations Catalyzed by CO(II) Complexes of Pyridine–containing Copolymers.

J. Chem. Soc. Davey et al 1957 pp 1008–1015—196. Chalcones and Related Compounds. Part I, Preparation of Nitro–, Amino–, and Halogeno–chalcones.

Baldoli et al, Tetrahedron, vol. 46, No. 23, 1990, pp. 7823–7830; XP002201568.

Baumstark et al, Journal of Organic Chemistry, vol. 58, No. 26, 1993, pp. 7615–7618; XP002201569.

Tishchenko, Zh. Org. Khim., vol. 7, No. 7, 1971, pp. 1410–1414; XP002201570 abstract.

*Primary Examiner*—Ba K. Trinh
(74) *Attorney, Agent, or Firm*—Nixon & Vanderhye P.C.

(57) ABSTRACT

An optically active epoxypropionate derivative of the following formula (1):

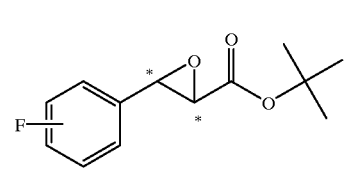

(1)

wherein symbol * represents optically active carbon. Also disclosed is an optically active epoxypropionate derivative of the following formula (2):

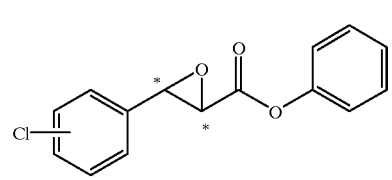

(2)

wherein symbol * represents optically active carbon.

11 Claims, No Drawings

OPTICALLY ACTIVE EPOXYPROPIONATE DERIVATIVE, INTERMEDIATE THEREOF AND PROCESSES FOR THEIR PRODUCTION

The present invention relates to an optically active epoxypropionate derivative, an intermediate thereof and processes for their production. The optically active propionate derivative of the present invention is useful as an intermediate for the preparation of pharmaceuticals or agricultural chemicals.

As an optically active propionate derivative, one having a methoxy group introduced at the 4-position (the p-position) of a phenyl ring, is known as an intermediate for the preparation of a known diltiazem (see, for example, JP-A-60-13776 and JP-A-6-287183). However, an optical active epoxypropionate derivative of the following Formula (1):

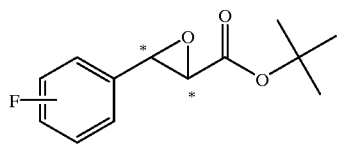

(1)

wherein symbol * represents optically active carbon, or the following Formula (2):

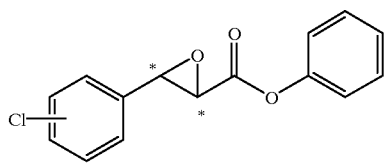

(2)

wherein symbol * represents optically active carbon, has not been known.

Further, as a process for producing an optically active epoxypropionate derivative, a process for separating an optically active substance from a racemic modification by optical resolution is known, but a process for producing such a compound by an asymmetric synthesis has not been known.

Under these circumstances, the present invention has been made, and it is an object of the present invention to provide a novel optically active epoxypropionate derivative expected to be an intermediate for the preparation of pharmaceuticals or agricultural chemicals, an intermediate for its preparation and a process for their production.

The present inventors have conducted an extensive study to prepare a novel optically active epoxypropionate derivative expected to be an intermediate for the preparation of pharmaceuticals or agricultural chemicals and as a result, have found the optically active epoxypropionate derivative of the above Formula (1) or (2) and an optically active epoxyenone derivative of the following Formula (3):

(3)

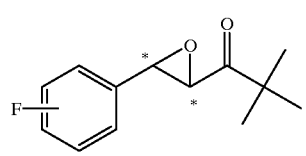

wherein symbol * represents optically active carbon, which is an intermediate for the preparation of the compound of the above formula (1). And, they have found processes for their production by asymmetric syntheses. The present invention has been accomplished on the basis of these discoveries.

Namely, the present invention provides the optically active epoxypropionate derivative of the above Formula (1) or (2), the optically active epoxyenone derivative of the above Formula (3) and processes for their production.

Now, the present invention will be described in detail with reference to the preferred embodiments.

The optically active epoxypropionate derivative of the above Formula (1) of the present invention is specifically t-butyl(2S, 3R)-trans-2,3-epoxy-3-(4'-fluorophenyl) propionate, t-butyl(2S, 3R)-trans-2,3-epoxy-3-(3'-fluorophenyl) propionate, t-butyl(2S, 3R)-trans-2,3-epoxy-3-(2'-fluorophenyl) propionate, t-butyl(2R, 3S)-trans-2,3-epoxy-3-(4'-fluorophenyl) propionate, t-butyl(2R, 3S)-trans-2,3-epoxy-3-(3'-fluorophenyl) propionate, or t-butyl(2R, 3S)-trans-2,3-epoxy-3-(2'-fluorophenyl) propionate.

The optically active epoxypropionate derivative of the above Formula (2) of the present invention is specifically phenyl trans-3-(2-chlorophenyl)-(2S, 3R)-epoxypropionate, phenyl trans-3-(3-chorophenyl)-(2S, 3R)-epoxypropionate, phenyl trans-3-(4-chlorophenyl)- (2S, 3R)-epoxypropionate, phenyl trans-3-(2-chlorophenyl)-(2R, 3S)-epoxypropionate, phenyl trans-3-(3-chlorophenyl)-(2R, 3S)-epoxypropionate, or phenyl trans-3-(4-chlorophenyl)-(2R, 3S)-epoxypropionate.

The optically active epoxyenone derivative of the above Formula (3) of the present invention is specifically (1R, 2S)-trans-1,2-epoxy-1-(4'-fluorophenyl)-4,4-dimethyl-pentan-3-one, (1R, 2S)-trans-1,2-epoxy-1-(3'-fluorophenyl)-4,4-dimethyl-pentan-3-one, (1R, 2S)-trans-1,2-epoxy-1-(2'-fluorophenyl)-4,4-dimethyl-pentan-3-one, (1S, 2R)-trans-1,2-epoxy-1-(4'-fluorophenyl)-4,4-dimethyl-pentan-3-one, (1S, 2R)-trans-1,2-epoxy-1-(3'-fluorophenyl)-4,4-dimethyl-pentan-3-one, or (1S, 2R)-trans-1,2-epoxy-1-(2'-fluorophenyl)-4,4-dimethyl-pentan-3-one.

The compound of the above Formula (1) of the present invention can be prepared by the following synthetic route using a known enone as the staring material, although the preparation is not particularly limited.

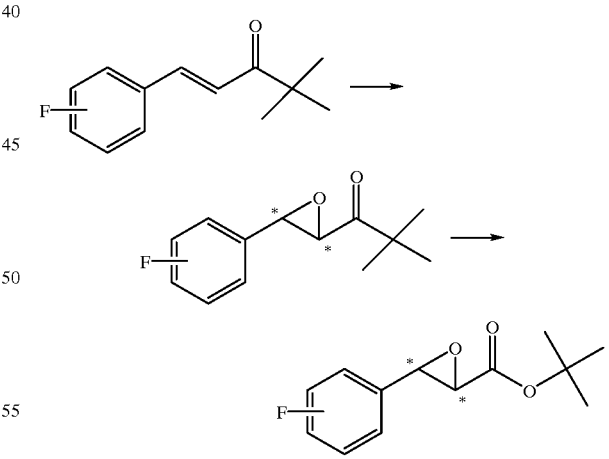

In the above formulae, symbol * represents optically active carbon.

Namely, the optically active epoxyenone derivative of the above Formula (3) is prepared by asymmetric epoxidation of an enone, and further, the derivative is oxidized with an oxidizing agent, whereby the optically active epoxypropionate derivative of the above Formula (1) is prepared.

Further, the compound of the above Formula (2) of the present invention can be prepared by the following route by asymmetric epoxidation of an enone using a known enone as the starting material, although the preparation is not particularly limited.

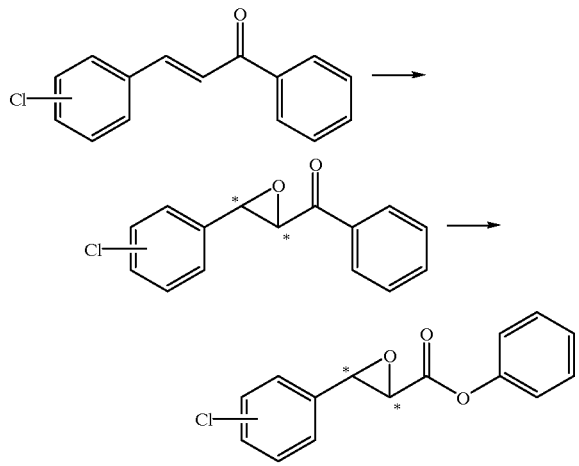

In the formulae, symbol * represents optically active carbon.

As a catalyst to be used for the asymmetric epoxidation reaction of the present invention, any asymmetric epoxidation catalyst for enones can be used. However, it is preferred to employ a catalyst comprising:

(A) an optically active binaphthol,
(B) lanthanum triisopropoxide,
(C) triphenylphosphine oxide, and
(D) cumene hydroperoxide (hereinafter referred to as CMHP) or tert-butyl hydroperoxide (hereinafter referred to as TBHP), since the substrate selectivity is low, and it provides good yield and a high optical purity. Here, in the present invention, the optically active binaphthol is specifically (R)-(+)-1,1'-bi-2-naphthol (hereinafter referred to as (R)-binaphthol) or (S)-(−)-1,1'-bi-2-naphthol (hereinafter referred to as (S)-binaphthol).

With respect to the constituting proportions of the above-mentioned catalyst components, theoretically, the respective constituting components may be present in equivalent amounts. However, in order to let the catalyst form stably in the reaction system, (A) the binaphthol is usually from 1 to 3 mols, preferably from 1 to 1.5 mols, (C) the triphenylphosphine oxide is usually from 0.1 to 10 mols, preferably from 1 to 10 mols, and (D) CMHP or TBHP is usually from 1 to 20 mols, preferably from 1 to 10 mols, per mol of (B) the lanthanum triisopropoxide.

In the asymmetric epoxidation reaction of the present invention, it is preferred that the above catalyst components are preliminarily formulated into a catalyst solution in the reaction system and then used for the epoxidation reaction of an enone.

Further, in the asymmetric epoxidation reaction of the present invention, if (R)-binaphthol is employed, the steric configuration at the 2-position (α-position of carbonyl group) and 3-position (β-position of carbonyl group) of the epoxyenone of the present invention will be (2S, 3R), and if (S)-binaphthol is employed, it will be (2R, 3S).

In the asymmetric epoxidation reaction of the present invention, the amount of the catalyst is not particularly limited, but it is usually within a range of from 0.01 to 50 mol %, more preferably within a range of from 0.1 to 25 mol %, based on the molar amount of the lanthanum isopropoxide, relative to the substrate subjected to the reaction.

The solvent useful for the asymmetric epoxidation reaction of the present invention may be any solvent so long as it is a solvent inert to the catalyst and to the epoxidation reaction. However, from the viewpoint of the stability of the catalyst and the reaction efficiency of the epoxidation reaction, an ether type solvent such as dimethyl ether, diisopropyl ether, 1,2-dimethoxyethane or tetrahydrofuran (hereinafter referred to as THF), is preferred, and among them, it is THF that gives the highest results. Such a solvent can be used also as a solvent for the preparation of the above catalyst solution.

The amount of the solvent is usually from 2 to 200 times, preferably from 5 to 100 times, by weight, to the enone to be subjected to the reaction.

In the asymmetric epoxidation reaction of the present invention, a complex catalyst comprising:

(A) an optically active binaphthol,
(B) lanthanum triisopropoxide,
(C) triphenylphosphine oxide, and
(D) cumene hydroperoxide or tert-butyl hydroperoxide, presents a higher optical activity to the product.

In the preparation of the complex catalyst, the time for formation of the catalyst varies depending upon the proportions of the components constituting the catalyst, selection of the oxidizing agent, the type of the solvent and the concentration of the catalyst. However, the complex catalyst can be formed usually by maintaining the mixture for from 0.5 to 4 hours within a range of from −50° C. to 100° C., and the solution after the formation of the complex shows a color of yellowish green to deep green.

As TBHP to be used as an oxidizing agent in the asymmetric epoxidation reaction of the present invention, a commercially available solution in e.g. decane may be used as it is, or it may be extracted by toluene from a 70% or 90% aqueous solution, followed by drying over e.g. magnesium sulfate, and then may be used in the present invention. Further, as CMHP, a commercially available 80 wt % product may be used after purification or as it is without purification. Preferably, purified or commercially available CMHP is employed, whereby a pure optically active substance can be obtained.

For the asymmetric epoxidation reaction of the present invention, the above enone is added to the preliminarily prepared catalyst solution, and then CMHP or TBHP is supplied to carry out the reaction. With respect to the supply rate of the oxidizing agent, the supply is carried out under such a condition that the oxidizing agent will not be in large excess in the system. Specifically, the supply rate is determined by measuring the reaction rate in the actual system, whereupon the supply is carried out. If the supply rate is higher than the reaction rate, the yield may decrease, and if it is lower, the optical purity may decrease.

In the asymmetric epoxidation reaction of the present invention, the amount of the oxidizing agent should theoretically be sufficient with an equivalent amount to the enone subjected to the reaction, as the sum of the amount used for forming the catalyst and the amount added during the reaction. However, in order to complete the reaction, it is preferably used in an amount of at least 1.1 times by mol.

The reaction temperature in the asymmetric epoxidation reaction of the present invention varies depending upon the difference in the substrate of the enone, but it is usually within a range of from −50° C. to 100° C. With respect to the reaction time, the reaction is completed usually within 48 hours.

In the asymmetric epoxidation reaction of the present invention, zeolite may be used, as the case requires, for the purpose of removing water in the system during the preparation of the catalyst and during the reaction or for the purpose of accelerating the catalyst-forming reaction or the epoxidation reaction. The zeolite may be used in any ratio to the enone, but it is used usually in an amount of from about 10 mg to 2 g per mmol of the enone. With respect to the type of the zeolite, various zeolites can be used including type A zeolites represented by molecular sieves 3A, 4A, and 5A, molecular sieve 13X, type Y zeolite and type L zeolite. Among these, molecular sieve 4A is preferred.

After completion of the epoxidation reaction of the present invention, post treatment for purification by e.g. column chromatography is carried out, whereby the optically active epoxyenone of the above Formula (3) or (4) can be obtained in good yield with a high optical purity.

The process of obtaining the optically active epoxypropionate of the present invention is not particularly limited. For example, the optically active epoxyenone obtained by the above method is oxidized by a Baeyer-Villiger reaction to obtain the desired product.

As the oxidizing agent to be used for the Baeyer-Villiger reaction of the present invention, any peracid or peroxide may be employed. However, specifically, potassium persulfate, hydrogen peroxide, perbenzoic acid, m-chloroperbenzoic acid, CMHP or TBHP may, for example, be mentioned. The reaction is carried out usually within a temperature range of from 0° C. to 150° C. for from 1 to 48 hours to obtain the desired product. Further, depending upon the type of the peracid or peroxide, an alkali metal hydroxide such as sodium hydroxide, potassium hydroxide or lithium hydroxide may be used in combination, and the reaction may be carried out in a water/alcohol solvent.

The amount of the oxidizing agent to be used in the Baeyer-Villiger reaction of the present invention is usually from 1 to 10 times by mol, preferably from 2 to 5 times by mol, relative to the epoxyenone subjected to the reaction.

After completion of the Baeyer-Villiger reaction of the present invention, the peracid or peroxide is deactivated, and then, the optically active epoxypropionate derivative as the desired product, can be obtained by extraction with an organic solvent, followed by drying, concentration and purification by column chromatography.

The optically active epoxypropionate derivative of the present invention has a high optical purity and is expected to be an important intermediate for various pharmaceuticals or agricultural chemicals.

Now, the present invention will be described in further detail with reference to Examples. However, it should be understood that the present invention is by no means restricted to such specific Examples.

Further, for the analyses of the products, the following equipments were employed.
Measurement of optical rotation
SEPA-300, manufactured by HORIBA K. K. was used.
Measurement of melting point
MP-500D manufactured by Yanako K. K. was used.
Measurements of $^1$H-NMR and $^{13}$C-NMR
Gemini-200, manufactured by Varian, was used (200 MHz).
Measurement of MASS
M-80B, manufactured by Hitachi, was used.
Measurement of IR
200OFT-IR, manufactured by Perkin Elmer, was used.
Determination of optical purity
High performance liquid chromatography having chiral column AD of Daicel K. K. mounted, was used, and the measurement was carried out at a flow rate of 1 ml/min with an eluent of hexane/i-PrOH=95/5 (vol/vol).

EXAMPLE 1

Preparation of trans-(1R, 2S)-1,2-epoxy-1-(2'-fluorophenyl)-4,4-dimethylpentan-3-one

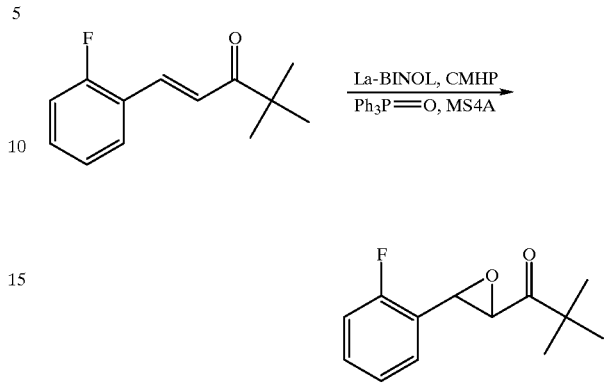

Into a 50 ml eggplant type flask containing a magnetic stirrer, molecular sieve 4A (687 mg, product preliminarily dried for 4 hours at 180° C. under reduced pressure) was put and heated for 3 minutes by a heat gun under reduced pressure by means of a vacuum pump and dried. After cooling to room temperature, triphenylphosphine oxide (574 mg, 2.06 mmol) and (R)-binaphthol (197 mg, 0.69 mmol) were introduced, and the reaction system was flushed with nitrogen gas. Then, THF (20 ml) was added thereto, followed by stirring for 5 minutes for dissolution. Then, the mixture was added to a THF solution (10 ml) of lanthanum isopropoxide (La(OiPr)$_3$, 217 mg, 0.69 mmol), followed by stirring for 1 hour. Further, CMHP (80%, 127 μl, 0.69 mmol) was added, followed by stirring for 1 hour to obtain a catalyst solution.

After confirming that the catalyst solution was colored yellowish green, a THF (15 ml) solution of trans-1-(2'-fluorophenyl)-4,4-dimethyl-1-penten-3-one (2.84 g, 13.7 mmol) was added thereto to initiate the reaction. After the initiation of the reaction, CMHP (80%, 3.17 ml, 17.2 mmol) was dropwise added over a period of 20 hours, followed by stirring for 88 hours. Here, the supply rate of CMHP was set to be 20 hours based on the conversion rate of 5.0%/hr as a result of the measurement of the rate by an equivalent reaction.

After completion of the reaction, 5.0 g of silica gel and 20 ml of methanol were added, followed by stirring for 2 hours and then by filtration, concentration and purification by a silica gel column (hexane/ethyl acetate=9/1) to obtain trans-(1R, 2S)-1,2-epoxy-1-(2'-fluorophenyl)-4,4-dimethylpentan-3-one (1.62 g) as white crystals (yield: 53%, optical purity: at least 99 ee %).

Melting point: 61.0–62.5° C.

$^1$H-NMR (CDCl$_3$) δ7.03–7.39(m, 4H), 4.10(d, 1H, J=1.8 Hz), 3.84(d, 1H, J=1.8 Hz), 1.25 (s, 9H)

$^{13}$C-NMR (CDCl$_3$) δ207.8, 161.4 (J=246.4 Hz), 130.1 (J=8.1 Hz), 126.2 (J=3.5 Hz), 124.5 (J=3.5 Hz), 123.2 (J=12.9 Hz), 115.4 (J=20.2 Hz), 58.1, 54.3, 43.7, 25.7

IR (KBr; υ cm$^{-1}$) 2978, 2935, 1710, 1619, 1587, 1494, 1458, 1416, 1248, 1217, 1099, 1077, 1004, 895, 822, 764, 590, 518

EI-MS(m/z) 222 (M$^+$)

Specific rotation (c=1.03 CHCl$_3$) $[\alpha]^{28}_D$=+191

EXAMPLE 2

Preparation of trans-(1R, 2S)-1,2-epoxy-1-(3'-fluorophenyl)-4,4-dimethylpentan-3-one

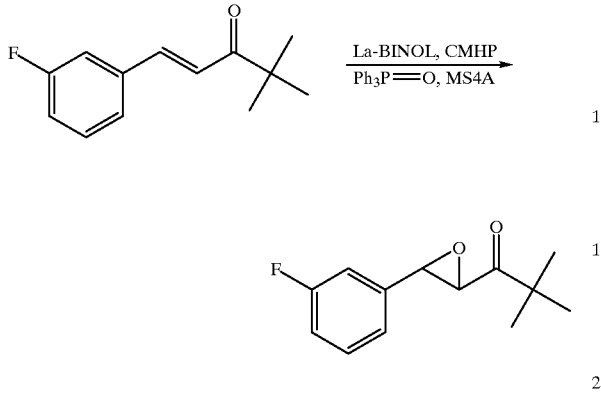

Into a 50 ml eggplant type flask, molecular sieve 4A (1.32 g) was put, and heated and dried by a heat gun for 3 minutes under reduced pressure by means of a vacuum pump. After cooling to room temperature, triphenylphosphine oxide (1.10 g, 3.97 mmol) and (R)-binaphthol (379 mg, 1.32 mmol) were introduced, and the reaction system was flushed with nitrogen gas. Then, THF (30 ml) was added, followed by stirring for 5 minutes for dissolution. Then, the mixture was added to a THF solution (30 ml) of lanthanum isopropoxide (La(OiPr)$_3$, 418 mg, 1.32 mmol), followed by stirring for 1 hour. Further, CMHP (80%, 244 μl, 1.32 mmol) was added thereto, followed by stirring for 1 hour to obtain a catalyst solution.

After confirming that the catalyst solution was colored yellowish green, a THF (27 ml) solution of trans-1-(3'-fluorophenyl)-4,4-dimethyl-1-penten-3-one (5.46 g, 26.4 mmol) was added to initiate the reaction. After the initiation of the reaction, CMHP (80%, 6.11 ml, 33.1 mmol) was dropwise added over a period of 12 hours, followed by stirring for 127 hours. Here, the supply rate of CMHP was set to be 12 hours, based on a conversion rate of 8.2%/hr as a result of the measurement of the rate by an equivalent reaction.

After completion of the reaction, 5.0 g of silica gel and 20 ml of methanol were added, followed by stirring for 2 hours and then by filtration, concentration and purification by a silica gel column (hexane/ethyl acetate=9/1) to obtain trans-(1R, 2S)-1,2-epoxy-1-(3'-fluorophenyl)-4,4-dimethylpentan-3-one (3.04 g) as white crystals (yield: 52%, optical purity: at least 99 ee %).

Melting point: 68.0 to 69.5° C.

$^1$H-NMR (CDCl$_3$) δ6.97–7.40 (m, 4H), 3.86 (d, 1H, J=1.8 Hz), 3.81 (d, 1H, J=1.8 Hz), 1.24 (s, 9H)

$^{13}$C-NMR (CDCl$_3$) δ207.7, 163.1 (J=245.7 Hz), 138.3 (J=7.5 Hz), 130.4 (J=8.1 Hz), 121.5 (J=2.9 Hz), 116.0 (J=25.3 Hz), 112.4 (J=22.7 Hz), 59.0, 58.6, 43.6, 25.7

IR (KBr; υ cm$^{-1}$) 2975, 2937, 1705, 1616, 1592, 1464, 1412, 1397, 1275, 1230, 1140, 1075, 1005, 869, 775, 689, 580, 523

EI-MS(m/z) 222 (M$^+$)

Specific rotation (c=1.015 CHCl$_3$) [α]$^{27}_D$=+236

EXAMPLE 3

Preparation of trans-(1R, 2S)-1,2-epoxy-1-(4'-fluorophenyl)-4,4-dimethylpentan-3-one

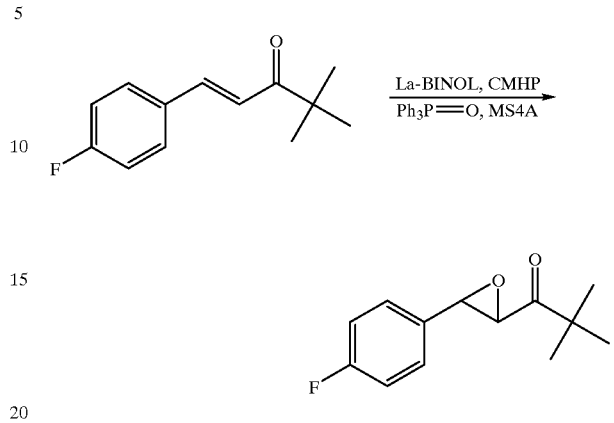

Into a 50 ml eggplant type flask, molecular sieve 4A (869 mg) was put, and heated and dried by a heat gun for 3 minutes under reduced pressure by means of a vacuum pump. After cooling to room temperature, triphenylphosphine oxide (725 mg, 2.61 mmol) and (R)-binaphthol (249 mg, 0.87 mmol) were introduced, and the reaction system was flushed with nitrogen gas. Then, THF (25 ml) was added, followed by stirring for 5 minutes for dissolution. Then, the mixture was added to a THF solution (35 ml) of lanthanum isopropoxide (La(OiPr)$_3$, 275 mg, 0.87 mmol), followed by stirring for 1 hour. Further, CMHP (80%, 321 μl, 1.74 mmol) was added, followed by stirring for 1 hour to obtain a catalyst solution.

After confirming that the catalyst solution was colored yellowish green, a THF (45 ml) solution of trans-1-(4'-fluorophenyl)-4,4-dimethyl-1-penten-3-one (3.60 g, 17.4 mmol) was added to initiate the reaction. After the initiation of the reaction, CMHP (80%, 3.85 ml, 20.9 mmol) was dropwise added over a period of 12 hours, followed by stirring for 8 hours. Here, the supply rate of CMHP was set to be 12 hours based on a conversion rate of 8.5%/hr as a result of the measurement of the rate by an equivalent reaction.

After completion of the reaction, 5.0 g of silica gel and 20 ml of methanol were added, followed by stirring for 2 hours and then by filtration, concentration and purification by a silica gel column (hexane/ethyl acetate=9/1) to obtain trans-(1R, 2S)-1,2-epoxy-1-(4'-fluorophenyl)-4,4-dimethylpentan-3-one (1.73 g) as white crystals (yield: 45%, optical purity: 99 ee %)

Melting point: 65.8–66.5° C.

$^1$H-NMR (CDCl$_3$) δ7.02–7.32 (m, 4H), 3.85 (d, 1H, J=1.8 Hz), 3.82 (d, 1, J=1.8 Hz), 1.24 (s, 9H)

$^{13}$C-NMR (CDCl$_3$) δ207.9, 163.1 (J=246.5 Hz), 130.0 (J=144.6 Hz), 127.4 (J=8.2 Hz), 115.8 (J=21.9 Hz), 59.1, 58.7, 43.6, 25.7

IR (KBr; ν cm$^{-1}$) 2974, 2936, 1714, 1606, 1514, 1478, 1436, 1398, 1223, 1157, 1075, 1004, 892, 842, 786, 555, 528

EI-MS(m/z) 222 (M$^+$)

Specific rotation (c=1.035 CHCl$_3$) [α]$^{28}_D$=+185

EXAMPLE 4

Preparation of tert-butyl (2S, 3R)-trans-2,3-epoxy-3-(2'-fluorophenyl)propionate

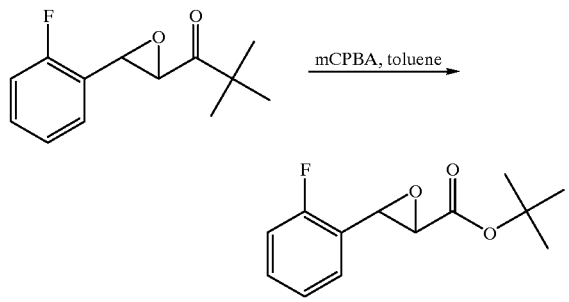

In a 100 ml eggplant type flask equipped with a magnetic stirrer, trans-(1R, 2S)-1,2-epoxy-1-(2'-fluorophenyl)-4,4-dimethylpentan-3-one (500 mg, 2.25 mmol) obtained in Example 1 and m-chloroperbenzoic acid (80% mCPBA, 1.94 g, 9.00 mmol) were dissolved in 15 ml of toluene, followed by heating on an oil bath to carry out the reaction at 90° C. for 19 hours. The reaction solution was cooled to room temperature, and then by a silica gel short column, the precipitated substance and the adsorbed substance were removed, followed by washing with 100 ml of dichloromethane. The obtained eluate was concentrated and dried under reduced pressure to obtain a residue, which was then purified by a silica gel column (hexane/ethyl acetate=9/1) to obtain tert-butyl trans-(2S, 3R)-2,3-epoxy-3-(2'-fluorophenyl)propionate (307 mg) as a colorless transparent oily substance (yield: 57%, optical purity: at least 99 ee %).

$^1$H-NMR (CDCl$_3$) δ7.02–7.37 (m, 4H), 4.30 (d, 1H, J=1.8H z), 3.41 (d, 1H, J=1.8 Hz), 1.52 (s, 9H)

$^{13}$C-NMR (CDCl$_3$) δ166.9, 161.6 (J=246.7 Hz), 130.1 (J=8.1 Hz), 126.3 (J=3.3 Hz), 124.4 (J=3.6 Hz), 122.9 (J=12.6 Hz), 115.4 (J=20.7 Hz), 82.9, 56.7, 52.3, 28.0

IR (neat; ν cm$^{-1}$) 2982, 2936, 1746, 1620, 1590, 1496, 1459, 1424, 1370, 1343, 1307, 1253, 1226, 1158, 970, 895, 759

EI-MS (m/z) 238 (M$^+$)

Specific rotation (c=1. 100 CHCl$_3$) [α]$^{28}_D$=+119

EXAMPLE 5

Preparation of tert-butyl (2S, 3R)-trans-2,3-epoxy-3-(3'-fluorophenyl)propionate

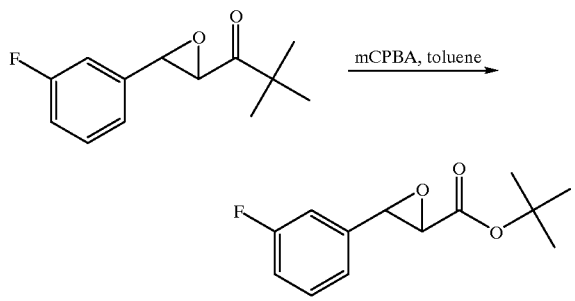

In a 100 ml eggplant type flask equipped with a magnetic stirrer, trans-(1R, 2S)-epoxy-1-(3-fluorophenyl)-4,4-dimethylpentan-3-one (514 mg, 2.31 mmol) obtained in Example 2 and m-chloroperbenzoic acid (80% mCPBA, 1.40 g, 6.47 mmol) were dissolved in 15 ml of toluene, followed by heating on a hot bath to carry out the reaction at 90° C. for 46 hours. The reaction solution was cooled to room temperature, and then, by a silica gel short column, the precipitated substance and the adsorbed substance were removed, followed by washing with 100 ml of dichloromethane. The eluate was concentrated and dried under reduced pressure to obtain a residue, which was then purified by a silica gel column (hexane/ethyl acetate=9/1) to obtain tert-butyl trans-(2S, 3R)-2,3-epoxy-3-(3'-fluorophenyl) propionate (178 mg) as a colorless transparent oily substance (yield: 32%, optical purity: at least 99%).

$^1$H-NMR (CDCl$_3$) δ6.94–7.38 (m, 4H), 4.02 (d, 1H, J=1.8 Hz), 3.37 (d, 1H, J=1.8 Hz), 1.52 (s, 9H)

$^{13}$C-NMR (CDCl$_3$) δ166.8, 163.1 (J=246.7 Hz), 138.1 J=7.4 Hz), 130.3 (J=8.2 Hz), 121.8 (J=2.9 Hz), 115.9 (J=21.3 Hz), 112.7 (J=22.7 Hz), 82.9, 57.5, 56.9, 28.0

IR (neat; ν cm$^{-1}$) 2982, 2937, 1745, 1593, 1456, 1370, 1341, 1237, 1157, 971, 962, 875, 779

EI-MS(m/z) 238 (M$^+$)

Specific rotation (c=1.205 CHCl$_3$) [α]$^{28}_D$=+150

EXAMPLE 6

Preparation of tert-butyl (2S, 3R)-trans-2,3-epoxy-3-(4'-fluorophenyl)propionate

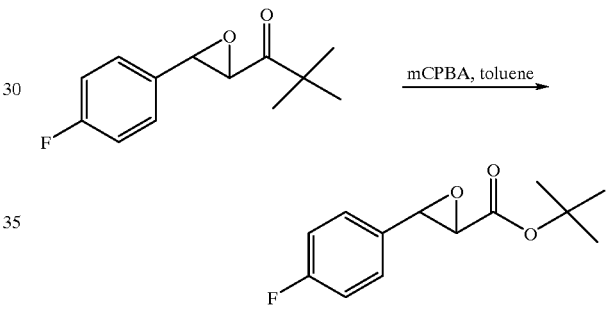

In a 100 ml eggplant type flask equipped with a magnetic stirrer, trans-(1R, 2S)-epoxy-1-(4'-fluorophenyl)-4,4-dimethylpentan-3-one (498 mg, 2.24 mmol) obtained in Example 3 and m-chloroperbenzoic acid (80% mCPBA, 1.93 g, 8.96 mmol) were dissolved in 15 ml of toluene, followed by heating to carry out the reaction at 90° C. for 19 hours. The reaction solution was cooled to room temperature and then, by a silica gel short column, the precipitated substance and the adsorbed substance were removed, followed by washing with 100 ml of dichloromethane. The eluate was concentrated and dried under reduced pressure to obtain a residue, which was then purified by a silica gel column (hexane/ethyl acetate=9/1) to obtain tert-butyl trans-(2S, 3R)-2,3-epoxy-3-(4'-fluorophenyl)propionate (124 mg) as white crystals (yield: 23%, optical purity: at least 99 ee %).

Melting point: 48.0–49.0° C.

$^1$H-NMR (CDCl$_3$) δ7.01–7.31 (m, 4H), 4.01 (d, 1H, (J=8 Hz), 3.37 (d, 1H, J=1.8 Hz), 1.52 (s, 9H)

$^{13}$C-NMR (CDCl$_3$) δ167.0, 163.1 (J=246.2 Hz), 131.1 (J=2.9 Hz), 127.7 (J=8.4 Hz), 115.7 (J=21.8 Hz), 82.8, 57.4, 57.1, 28.0

IR (KBr; ν cm$^{-1}$) 2990, 2942, 1724, 1609, 1515, 1468, 1440, 1407, 1369, 1230, 1158, 970, 877, 841, 821, 792, 770, 696, 556, 530

EI-MS(m/z) 238 (M$^+$)

Specific rotation (c=1.030 CHCl$_3$) [α]$^{28}_D$=+142

EXAMPLE 7

Preparation of trans-3-(4-chlorophenyl)-(2S, 3R)-epoxy-1-phenylpropane-1-one

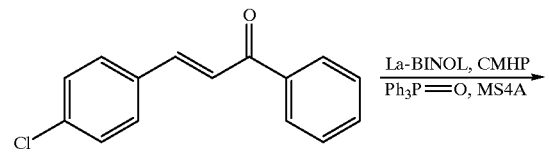

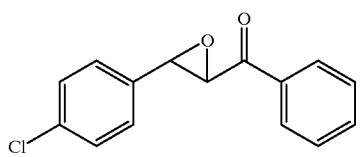

Into a 100 ml eggplant type flask containing a magnetic stirrer, molecular sieve 4A (827 mg, preliminarily dried produce under reduced pressure at 180° C. for 4 hours) was put, and heated and dried by a heat gun for 3 minutes under reduced pressure by means of a vacuum pump. After cooling to room temperature, triphenylphosphine oxide (345 mg, 1.24 mmol) and (R)-binaphthol (119 mg, 0.41 mmol) were introduced, and the reaction system was flushed with nitrogen gas. Then, THF (20 ml) was added, followed by stirring for 5 minutes for dissolution. Then, the mixture was added to a THF solution (20 ml) of lanthanum isopropoxide (La(OiPr)$_3$, 131 mg, 0.41 mmol), followed by stirring for 1 hour. Further, CMHP (80%, 153 μl, 0.83 mmol) was added, followed by stirring for 2 hours to obtain a catalyst solution.

After confirming that the catalyst solution was colored yellowish green, a THF (25 ml) solution of trans-4-chlorochalcone (2.01 g, 8.27 mmol) and CMHP (80%, 3.17 ml, 17.2 mmol), was dropwise added thereto over a period of 2 hours, followed by stirring for 1 hour.

After completion of the reaction, 2.0 g of silica gel and 20 ml of methanol were added, followed by stirring for 1 hour and then by filtration, concentration and purification by a silica gel column (hexane/ethyl acetate=6/1) to obtain trans-3-(4-chlorophenyl)-(2S, 3R)-epoxy-1-phenylpropane-1-one as white crystals (yield: 93%, optical purity: 99.6 ee %)

Melting point: 76–79° C.

$^1$H-NMR (CDCl$_3$) δ7.26–8.03 (m, 9H), 4.25 (d, 1H, J=1.8 Hz), 4.06 (d, 1H, J=1.8 Hz)

$^{13}$C -NMR (CDCl$_3$) δ192.7, 135.4, 134.9, 134.1, 129.0, 128.9, 128.3, 127.1, 125.4

IR (KBr; ν cm$^-$) 3069, 1683, 1597, 1495, 1446, 1339, 1237, 1090, 1006, 887, 843, 806, 705, 535, 476

EI-MS(m/z) 258 (M$^+$)

Elemental analysis C:69.4%, H:4.4%, Cl:13.5%

(calc. C:69.6%, H:4.3%, Cl:13.7%)

Specific rotation (c=1.035 CHCl$_3$) $[\alpha]^{28}{}_D$=+246°

EXAMPLE 8

Preparation of phenyl trans-3-(4-chlorophenyl)-(2S, 3R)-epoxypropionate

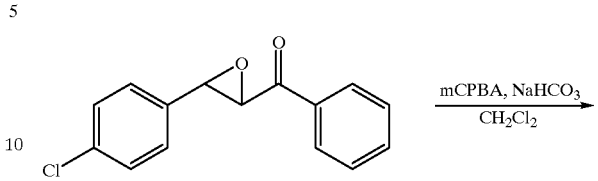

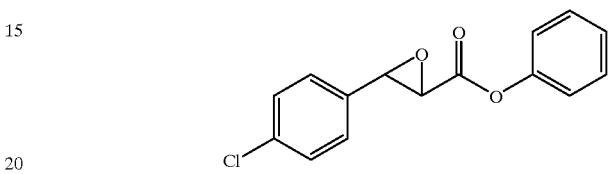

In a 100 ml eggplant type flask equipped with a magnetic stirrer, trans-3-(4-chlorophenyl)-(2S, 3R)-epoxy-1-phenylpropane-1-one (203 mg, 0.773 mmol) obtained in Example 1, m-chloroperbenzoic acid (80% mCPBA, 333 mg, 1.55 mmol) and sodium hydrogencarbonate (195 mg, 2.32 mmol) were dissolved in 10 ml of dichloromethane, followed by stirring under reflux for 6 hours to carry out the reaction. The reaction solution was cooled to room temperature, and then 20 ml of water and 20 ml of dichloromethane were added, whereupon the organic layer was separated and washed three times with 20 ml of water. The organic layer was dried over magnesium sulfate, and then, by a silica gel short column, the precipitated substance and the adsorbed substance were removed, followed by washing with 100 ml of dichloromethane. The eluate was concentrated and dried under reduced pressure to obtain a residue, which was then purified by a silica gel column (hexane/ethyl acetate=6/1) to obtain phenyl trans-3-(4-chlorophenyl)-(2S, 3R)-epoxypropionate as white crystals (yield: 46%, optical purity: at least 99 ee %).

Melting point: 107–110° C.

$^1$H-NMR (CDCl$_3$) δ7.14–7.45 (m, 9H), 4.24 (d, 1H, J=1.8 Hz), 3.69 (d, 1H, J=1.8 Hz)

$^{13}$C-NMR (CDCl$_3$) δ166.4, 150.2, 135.2, 134.5, 133.2, 130.3, 129.8, 129.6, 129.0, 127.9, 127.3, 126.4, 121.1, 57.7, 56.7

IR(KBr; ν cm$^{-1}$) 3068, 1752, 1598, 1591, 1487, 1430, 1397, 1267, 1201, 1164, 1090, 1013, 894, 831, 810, 751, 730, 688, 546, 479

EI-MS (m/z) 274 (M$^+$)

Elemental analysis C:65.4%, H:4.0%, Cl:13.2%

(calc. C:65.6%, H:4.0%, Cl:12.9%)

Specific rotation (c=0.760 CHCl$_3$) $[\alpha]^{28}{}_D$=+170°

The entire disclosure of Japanese Patent Application Nos. 2000-052268 filed on Feb. 24, 2000 and 2000-177153 filed on Jun. 8, 2000 including specification, claims, drawings and summary are incorporated herein by reference in its entirety.

What is claimed is:

1. An optically active epoxypropionate derivative of the following formula (1):

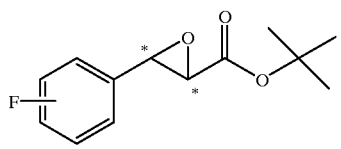

(1)

wherein symbol * represents optically active carbon.

2. An optically active epoxypropionate derivative of the following formula (2):

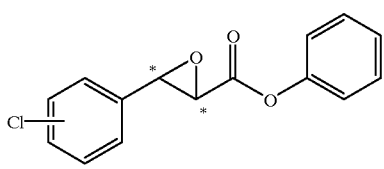

(2)

wherein symbol * represents optically active carbon.

3. A process for producing an optically active epoxypropionate derivative as defined in claim 1, which comprises oxidizing an optically active epoxyenone derivative of the following formula (3):

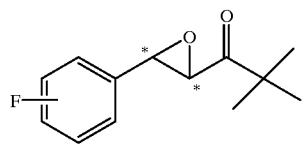

(3)

wherein symbol * represents optically active carbon, with an oxidizing agent.

4. An optically active epoxyenone derivative of the following formula (3):

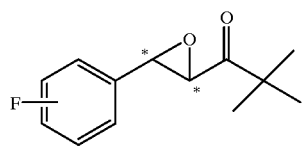

(3)

wherein symbol * represents optically active carbon.

5. A process for producing an optically active epoxypropionate derivative as defined in claim 2, which comprises oxidizing an optically active epoxyenone derivative of the following formula (4):

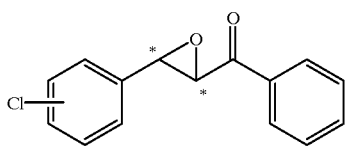

(4)

wherein symbol * represents optically active carbon, with an oxidizing agent.

6. A process for producing an optically active epoxyenone derivative as defined in claim 4, which comprises epoxidizing an enone derivative of the following formula (5):

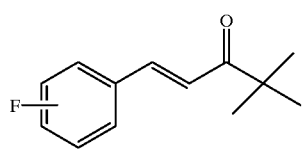

(5)

in the presence of an asymmetric catalyst.

7. A process for producing an optically active epoxyenone derivative as defined in claim 5, which comprises epoxidizing an enone derivative of the following formula (6):

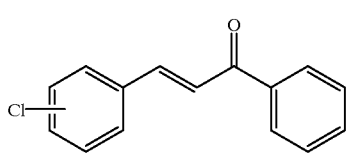

(6)

in the presence of an asymmetric catalyst.

8. The process for producing an optically active epoxyenone derivative according to claim 6, wherein the asymmetric catalyst comprises:

(A) an optically active binaphthol, (B) lanthanum triisopropoxide, (C) triphenylphosphine oxide, and (D) cumene hydroperoxide or tert-butyl hydroperoxide.

9. The process for producing an optically active epoxyenone derivative according to claim 7, wherein the asymmetric catalyst comprises:

(A) an optically active binaphthol, (B) lanthanum triisopropoxide, (C) triphenylphosphine oxide, and (D) cumene hydroperoxide or tert-butyl hydroperoxide.

10. The process for producing an optically active epoxyenone derivative according to claim 6, wherein the asymmetric catalyst comprises:

(A) (R)-(+)-1,1'-bi-2-binaphthol or (S)-(−)-1,1'-bi-2-naphthol, (B) lanthanum triisopropoxide, (C) triphenylphosphine oxide, and (D) cumene hydroperoxide or tert-butyl hydroperoxide.

11. The process for producing an optically active epoxyenone derivative according to claim 7, wherein the asymmetric catalyst comprises:

(A) (R)-(+)-1,1'-bi-2-binaphthol or (S)-(−)-1,1'-bi-2-naphthol, (B) lanthanum triisopropoxide, (C) triphenylphosphine oxide, and (D) cumene hydroperoxide or tert-butyl hydroperoxide.

* * * * *